(12) United States Patent
Tang et al.

(10) Patent No.: US 12,364,874 B2
(45) Date of Patent: Jul. 22, 2025

(54) OPHTHALMIC DEVICES FOR LIGHT THERAPY

(71) Applicant: Lumos Health Inc., Waterloo (CA)

(72) Inventors: Lucas Wen Tang, Waterloo (CA); Xin Yao, Nanjing (CN); Wei Zhang, Nanjing (CN)

(73) Assignee: Lumos Health Inc., Waterloo (CA)

( * ) Notice: Subject to any disclaimer, the term of this patent is extended or adjusted under 35 U.S.C. 154(b) by 0 days.

(21) Appl. No.: 18/618,295

(22) Filed: Mar. 27, 2024

(65) Prior Publication Data

US 2024/0226601 A1    Jul. 11, 2024

Related U.S. Application Data

(63) Continuation of application No. PCT/CN2023/085697, filed on Mar. 31, 2023.
(Continued)

(51) Int. Cl.
*A61N 5/06* (2006.01)

(52) U.S. Cl.
CPC .... *A61N 5/0618* (2013.01); *A61N 2005/0626* (2013.01); *A61N 2005/063* (2013.01); *A61N 2005/0634* (2013.01); *A61N 2005/0642* (2013.01); *A61N 2005/0648* (2013.01); *A61N 2005/0651* (2013.01); *A61N 2005/0659* (2013.01); *A61N 2005/0663* (2013.01);
(Continued)

(58) Field of Classification Search
CPC .......... A61N 5/0622; A61N 2005/0626; A61N 2005/0645; A61N 2005/0648; A61N 2005/0651; A61N 2005/0662; A61N 2005/0663; A61N 2005/0667

USPC .......................................................... 607/88
See application file for complete search history.

(56) References Cited

U.S. PATENT DOCUMENTS

| | | |
|---|---|---|
| 7,526,928 B1 | 5/2009 | Kearnes et al. |
| 9,335,604 B2 | 5/2016 | Popovich et al. |
| (Continued) | | |

FOREIGN PATENT DOCUMENTS

| | | |
|---|---|---|
| CN | 111624790 A | 9/2020 |
| FI | 129400 B | 1/2022 |
| WO | 2020070243 A1 | 4/2020 |

OTHER PUBLICATIONS

Groningen, "Pupillometry: Psychology, Physiology, and Function," Journal of Cognition, 1(1): 16, pp. 1-23. 2018.*
(Continued)

*Primary Examiner* — Ahmed M Farah

(57) ABSTRACT

Methods, systems, and devices related to light therapy using ophthalmic lenses are disclosed. In one example aspect, an optical device includes an ophthalmic lens and a frame comprising a frame front configured to support the ophthalmic lens. The frame includes two temples configured to allow a user to wear the optical device. The optical device includes a coating that is deposited in multiple sub-regions of the ophthalmic lens. The optical device includes a light source coupled to each of the two temples of the frame. The light source is controllable to emit light directed at the coating of the ophthalmic lens such that a portion of the light reflected by the multiple sub-regions of the ophthalmic lens forms a spectrum of light that has different wavelength bands corresponding to different therapeutical effects on the user.

21 Claims, 12 Drawing Sheets

Related U.S. Application Data

(60) Provisional application No. 63/362,374, filed on Apr. 1, 2022.

(52) U.S. Cl.
CPC ............... *A61N 2005/0666* (2013.01); *A61N 2005/0667* (2013.01)

(56) References Cited

U.S. PATENT DOCUMENTS

| | | | |
|---|---|---|---|
| 10,048,515 B2 | 8/2018 | Maitre et al. | |
| 10,571,699 B1 | 2/2020 | Parsons et al. | |
| 10,585,287 B2 | 3/2020 | Lee et al. | |
| 11,561,335 B2 | 1/2023 | Danziger et al. | |
| 2009/0204186 A1* | 8/2009 | Gruber | G02C 5/001 607/88 |
| 2012/0203310 A1* | 8/2012 | Pugh | A61N 5/0618 607/93 |
| 2015/0131047 A1* | 5/2015 | Saylor | G02B 1/11 351/44 |
| 2016/0187673 A1* | 6/2016 | Maitre | G02C 13/003 351/158 |
| 2016/0282532 A1* | 9/2016 | Le | C23C 14/228 |
| 2019/0258836 A1* | 8/2019 | Maurice | B29D 11/00009 |
| 2020/0094015 A1* | 3/2020 | Colbaugh | G16H 20/40 |
| 2020/0238101 A1 | 7/2020 | Schoutens | |
| 2021/0009849 A1* | 1/2021 | Tan | C09D 175/04 |
| 2021/0170195 A1 | 6/2021 | Wen et al. | |

OTHER PUBLICATIONS

China National Intellectual Property Administration (CNIPA), International Search Report and Written Opinion, PCT/CN2023/085697, Jun. 9, 2023.

Pierre-Alexander Blanche, et al., Holographic curved waveguide combiner for AR/HUD with 2D pupil expansion, Proceedings of SPIE—The International Society for Optical Engineering, Jan. 18, 2023, doi: 10.1117/12.2632864.

\* cited by examiner

800

US 12,364,874 B2

OPHTHALMIC DEVICES FOR LIGHT THERAPY

CROSS-REFERENCE

This application is a continuation and claims priority to International Application No. PCT/CN2023/085697, entitled "OPHTHALMIC DEVICES FOR LIGHT THERAPY", filed Mar. 31, 2023, which claims the benefit of U.S. Provisional Application No. 62/362,374, entitled "DICHROIC WAVELENGTH SELECTIVE COATINGS ON OPHTHALMIC LENSES FOR LIGHT THERAPY", filed on Apr. 1, 2022, the aforementioned applications are incorporated herein by reference in their entirety.

TECHNICAL FIELD

This patent document relates to systems, devices, and processes that implement wavelength selective techniques for performing different types of light therapies.

BACKGROUND

Ophthalmic devices (e.g., wearable glasses, contact lenses) are used to help correct visual refractive errors and help people see more clearly. Using materials with different refractive indices, these lenses bend light to help the eye properly focus images.

Advancements in technology bring about additional uses for ophthalmic devices, such as augmented reality, where films and coatings added to the lenses combined with artificial light help superposition images and videos over normal vision. Another application that expands of the ophthalmic lenses is the field of light therapy, where electronic light sources work together with the lenses to provide additional light to the user to provide treatment.

SUMMARY

This patent document describes, among other things, techniques that relate to ophthalmic devices that can provide different types of light therapies using a combination of light source(s) and coating regions on an ophthalmic lens. Some embodiments of the disclosed techniques can track the eye movement of the users and the environmental changes so as to help users, through the disclosed devices, adaptively select the light therapy that is best suitable for the user.

In one example aspect, an optical device includes an ophthalmic lens and a frame comprising a frame front configured to support the ophthalmic lens. The frame includes two temples configured to allow a user to wear the optical device. The optical device includes a coating that is deposited in multiple sub-regions of the ophthalmic lens. The multiple sub-regions are coated using different coating formulas and are located close to a peripheral of the ophthalmic lens and substantially outside of a field of view of a user of the optical device. The optical device includes a light source coupled to each of the two temples of the frame. The light source is controllable to emit light beams directed at the coating of the ophthalmic lens such that a portion of the light beams reflected by the multiple sub-regions of the ophthalmic lens forms a spectrum of light that has different wavelength bands corresponding to different therapeutical effects on the user. When the optical device is in operation, the spectrum of light is reflected into a pupil of the user as part of a light therapy session.

In another example aspect, a method of providing a light therapy to a user using an optical device is disclosed. The optical device comprises an ophthalmic lens, a coating deposited in multiple sub-regions of the ophthalmic lens, a frame with two temples, and a light source coupled to each of the two temples of the frame. The light source is controllable to emit light directed at the coating of the ophthalmic lens such that a portion of the light reflected by the multiple sub-regions of the ophthalmic lens forms a spectrum of light that has different wavelength bands corresponding to different therapeutical effects on the user, The method includes controlling, via a controller of the optical device, the light source to emit light to the ophthalmic lens such that a portion of the light is reflected by the ophthalmic lens into a pupil of the user, and communicating, via a communication model of the optical device, information about the ophthalmic lens and the light sources with a remote device to enable the user to track a performance of the light therapy on the remote device.

These, and other, aspects are described in the present document.

DETAILED DESCRIPTION

Wavelength based reflection and transmission can have special uses in light therapy. For example, different wavelengths of light can have different therapeutical effects on users. This patent document discloses techniques that can be implemented in various embodiments to provide an optical device to provide different types of light therapies (e.g., to help maintain the right sleep-wave cycle, regulate emotions, and/or boost performance) without introducing any disturbance to the user's daily activities. By reflecting certain wavelengths of light to the user while allowing other wavelengths to travel through, the disclosed techniques enable the reflection of desired wavelengths on the user and minimize interference with the user's normal vision. In some embodiments, wavelength-based reflection in different wavelength bands, through the deposition of dichroic coatings on ophthalmic lenses and/or waveguide design, can be implemented to achieve different therapeutical effects on the user. The disclosed techniques enable precise control of the wavelength and position of reflected light into the user's eyes to provide much finer control of stimulation of the photoreceptions within the eyes, allowing researchers/clinicians to optimize the effect of light therapy while not interfering with regular day to day activities of the user.

Figure 1A:
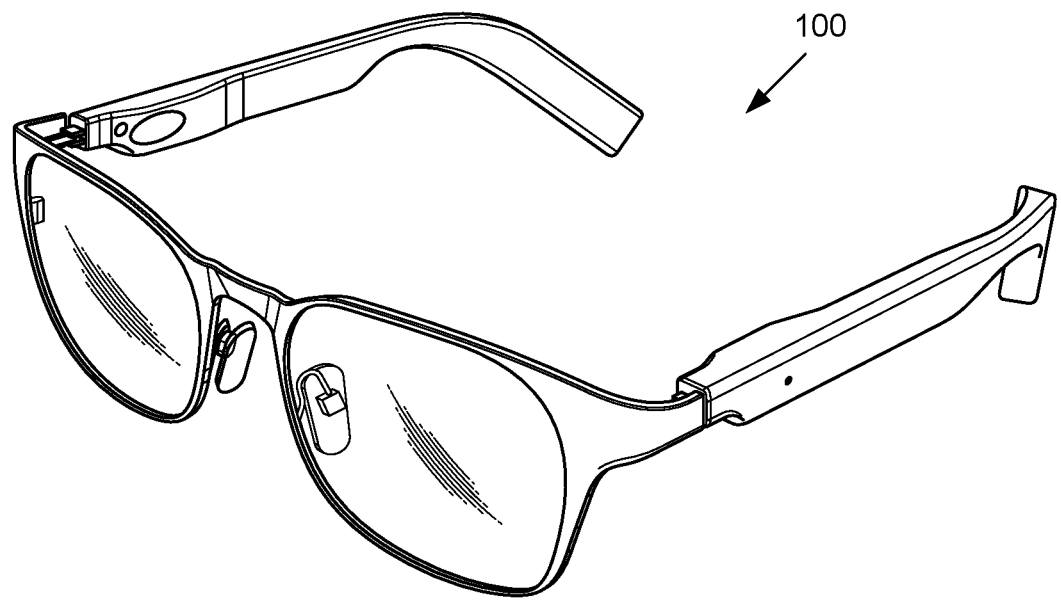
FIG. 1A illustrates an example optical device in accordance with one or more embodiments of the present technology.
Figure 1B:
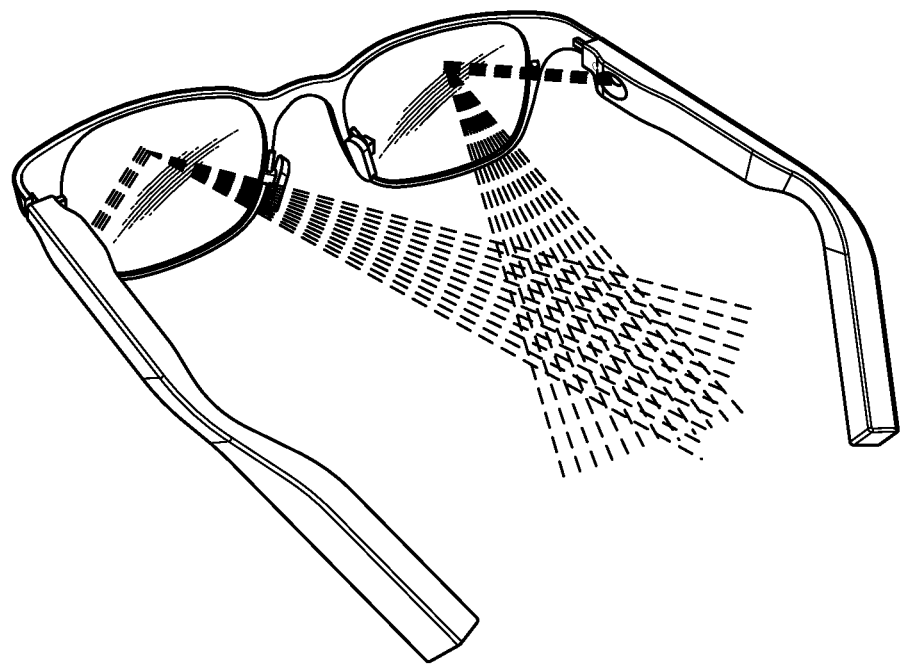
FIG. 1B illustrates another example optical device in accordance with one or more embodiments of the present technology.

FIGS. 1A-B illustrate an example optical device in accordance with one or more embodiments of the present technology. As shown in FIG. 1A, an optical device 100 can be implemented as a pair of spectacles or glasses. The examples shown in FIGS. 1A-B includes two ophthalmic lenses, but in some embodiments, one ophthalmic lens is used. The optical device includes a frame with a frame front configured to support one or more ophthalmic lenses. The frame also includes two temples that allow the user to wear the optical device on his or her face. In some embodiments, the frame is configured to reduce its size while not in use, such as a folding or collapsible frame.

The optical device is configured to produce a spectrum of light having different bands of wavelengths using a combination of light source(s) and reflective coating on the ophthalmic lens. For example, in the examples shown in FIGS. 1A-1B, a light source is embedded in one temple and are positioned behind a protective cover. The light source is controllable to emit a light beam. The emitted light beam is directed towards the ophthalmic lens and reflected by one or more sections of the ophthalmic lens to produce a spectrum of reflected light having different wavelengths that correspond to different therapeutical effects on the user. As shown in FIG. 1B, when the optical device is in operation, a portion of light from the light source is reflected by the ophthalmic lens into a pupil of the user.

Figure 2A:
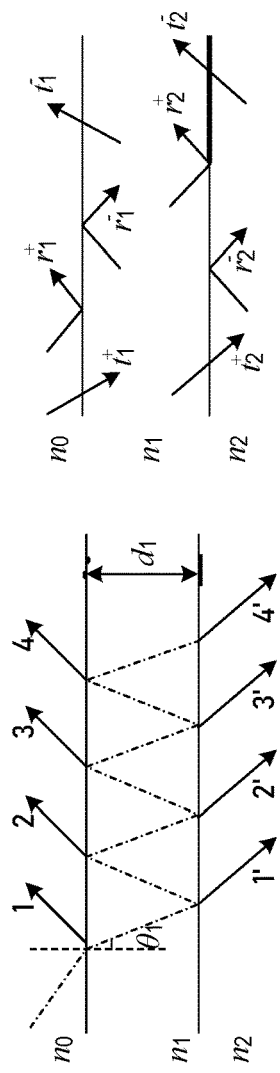
FIG. 2A is an example diagram illustrating how the reflected and transmitted light beams interact.

In some embodiments, the reflection of the light is achieved by depositing a dichroic coating on at least part of the lens. The principle of dichroic reflection is based on constructive and destructive interferences of multiple layers of thin film coatings. FIG. 2A is an example diagram illustrating how the reflected and transmitted light beams interact. When light strikes the surface of an interface of materials with different refractive indexes, a part of the light is reflected, and another part is transmitted. This effect is governed by the Fresnel equations. When the transmitted light strikes the next interface, the same phenomenon occurs. The reflected and transmitted lights from the interfaces can then interfere with each other based on the incidence angle, phase and wavelength of light.

Figure 2B:
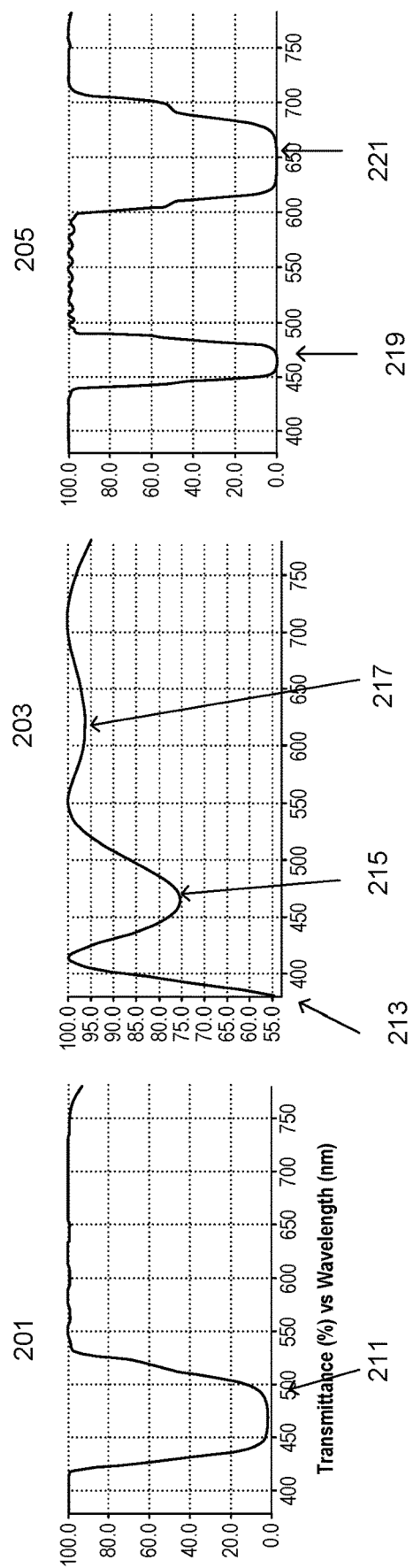
FIG. 2B illustrates examples of final transmission spectrum for dichroic coatings on ophthalmic lenses in accordance with one or more embodiments of the present technology.

Mathematical models and computer algorithms can be used to solve for a final reflected and transmitted spectrum curve when different layers, thickness and refractive indexes of coatings are accounted for. FIG. 2B illustrates examples of final transmission spectrum for dichroic coatings on ophthalmic lenses in accordance with one or more embodiments of the present technology. The final spectrum can be used for phototherapy purposes to either allow therapeutic wavelengths to be reflected or passed through. As shown in FIG. 2B, the final transmission spectrum can include different peaks in different wavelength bands that are suitable for different types of light therapies. One type of light therapy is bright light therapy related to circadian rhythm, sleep, and mental health. Circadian rhythm entrainment occurs when light is exposed to the intrinsically photosensitive retinal ganglion cells found at the back of the human eyes. The photopigment melanopsin present in these cells convert light to biological signals and is sensitive to wavelengths around 490 nm. Therefore, a high reflection or high transmission band that is centred proximal to the 490 nm wavelength is useful for bright light therapy applications as it allows the blocking or augmentation of relevant light to signal neurobiological changes. The plot 201 of FIG. 2B is an example of such transmission curve optimized for melanopsin effects, wherein a substantially amount of light in the wavelength band 450-490 nm (211) is reflected back to the user.

FIG. 2B also illustrates other examples of coating transmission curves that include multi wavelength transmission bands. Plot 203 of FIG. 2B illustrates a spectrum in which at least part (>30%) of a first band of light 213 under 420 nm is reflected and at least part (20%-25%) of a second band of light 215 between 450 to 470 nm is reflected. A third band of light 217 around 620 nm is also partially reflected (5%) back to the user. Plot 205 of FIG. 2B illustrates another spectrum in which a first band of light 219 (around 460 nm) and a second band of light 221 (around 650 nm) are fully reflected to the user. Using multiple wavelength bands, smart light therapy devices such as network-enabled glasses and/or spectacles can be implemented such that the dichroic coatings on the lenses of the spectacles can reflect light in different bands (e.g., from the environment or from electronic light sources embedded within the glasses) to achieve different therapeutical effects. Reflection of environment light can reduce the amount of light entering the user's eyes while reflection of the light sources of the optical device can increase the amount of light to the user.

The different bands of wavelengths are suitable for different types of treatments, such as treatment of seasonal depression, skin healing, and/or treatment of myopia. For example, blue light in the range of 450-550 nm, with a peak at 490 nm, targets the melanopsin photo pigment and has the highest impact on circadian rhythm and depression related symptoms. Green light, 465-625, peaking around 540 nm, has been shown to have an additional anti-anxiety effect. Red and yellow light (525-675 nm) has an impact at simulating the dawn and dusk response in humans. Furthermore, near infrared light has health benefits such as boosting blood flow and increasing cognitive function. Beyond circadian rhythm, light therapy with multiple wavelength ranges also have shown to treat eye diseases and skin problems. For example, UV (100-400 nm) and blue light (400-550) has been shown to promote regular eye development in children and prevent myopia.

In some embodiments, multiple coating operations can be performed with masking such that the ophthalmic lenses are partially coated or have different sections of the lenses with different coating formulas. Dichroic coatings can be performed by vapor deposition methods, where coating materials such has Silicone Oxide ($S_iO_2$), Magnesium Fluoride ($M_gF_2$), Titanium Oxide, Zirconium Oxides, and other optical oxides are deposited as thin films onto a substrate. Dichroic coatings can easily be over 30 layers of materials with various refractive indexes. The application of these coatings is complex and require special manufacturing considerations. In addition to dichroic coatings, antireflective coatings applied to lenses also employ a similar principle of using constructive and destructive interference to minimize reflection of light on lenses. The antireflective coatings often comprise 2-3 layers of material.

Figure 3A:
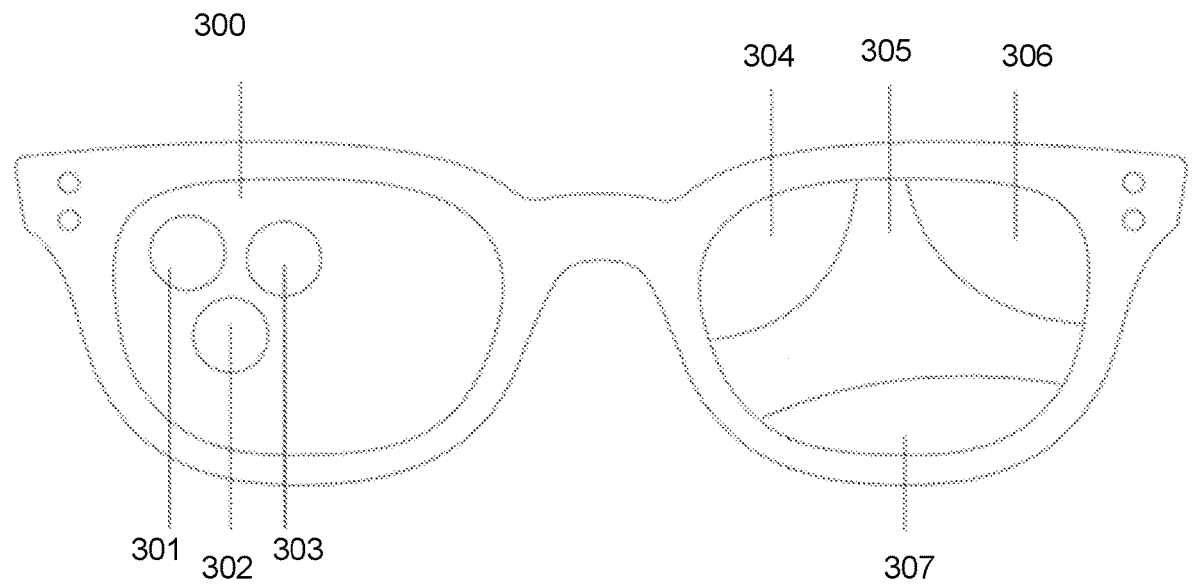
FIG. 3A illustrates an example coating on spectacle lenses in accordance with one or more embodiments of the present technology.
Figure 3B:
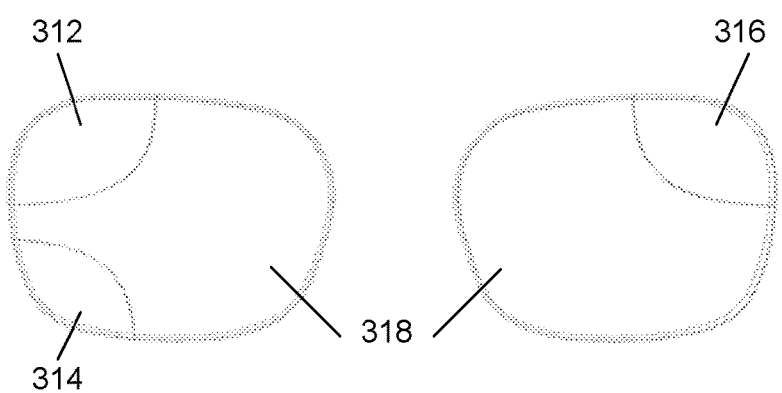
FIG. 3B illustrates another example coating on spectacle lenses in accordance with one or more embodiments of the present technology.

Different sections of the lens can be coated differently to reflect light from different light sources (e.g., lights coupled to the lens or environmental light) in different manners. FIG. 3A illustrates an example coating on the spectacle lenses in accordance with one or more embodiments of the present technology. In some embodiments, the spectacle lens 300 includes sections 301, 302, 303 that are at least partially coated. The sections 301, 302, and 303 can each be coated to work with a corresponding light source coupled to the frame to reflect light having a specific wavelength band. In some embodiments, the lens be divided into sections, e.g., section 304, 305, 306, 307, where at least some of the sections are coated differently from others. For example, section 305 can be coated with antireflective coating to minimize reflection of light in the field of view of the user. Sections 304, 306, and 307 can be coated using dichroic coating to reflect light in different wavelengths. FIG. 3B illustrates another example coating on the spectacle lenses in accordance with one or more embodiments of the present technology. Sections that are outside of the field of view of the user and are close to the peripheral of the lens (e.g., sections 312, 314, 316) are coated with dichroic coatings using different formulas to reflect lights in different wavelength bands. Sections that are inside the field of view of the user (e.g., 318) can be coated with antireflective coating to allow the light to pass through and to minimize reflection.

In some embodiments, the coating can be first applied to a substrate (e.g., a film or a piece of material smaller than the base lens) and the substrate is then assembled onto the lenses. Furthermore, the coating may be applied to surfaces on lens subdivisions, which are then joined together to form the full lens.

DETAILED DESCRIPTION

Figure 4A:
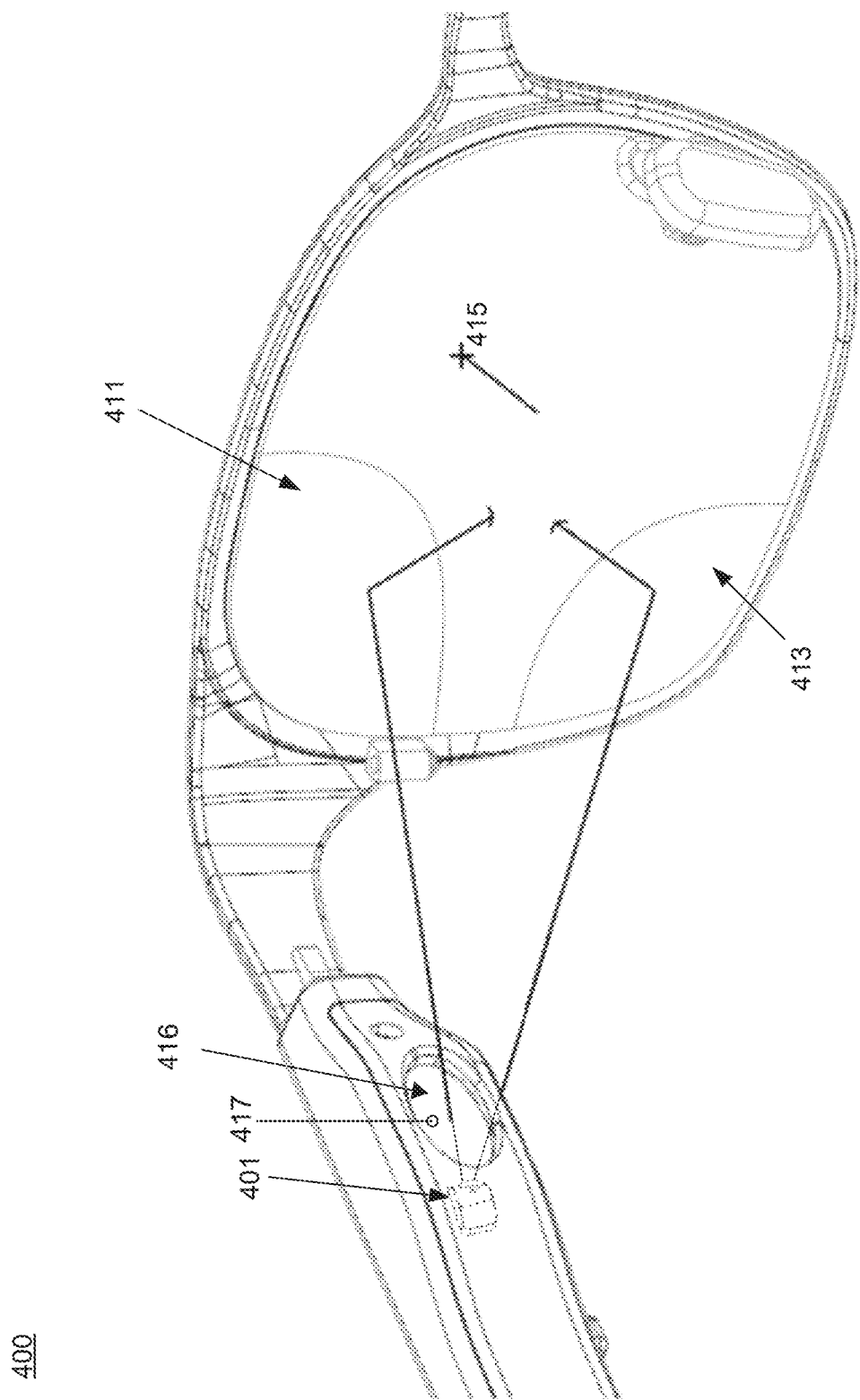
FIG. 4A illustrates an example configuration of a light source coupled to a temple of an optical device in accordance with one or more embodiments of the present technology.

FIG. 4A illustrates an example configuration 400 of a light source coupled to a temple of an optical device in accordance with one or more embodiments of the present technology. In this example, a light source 401 (represented in dotted line) is embedded in the temple of the optical device and positioned behind a protective cover 416. Light source 401 is configured to emit light to a first subregion 411 of the lens. Light source 401 is also configured to emit light to a second subregion 413 on the lens. In some embodiments, the protective cover 416 includes a filter 417. For example, the filter 417 can be Liquid Crystal Display (LCD) based to filter out unwanted light in selected locations before the light hits the ophthalmic lens. The filer 417 can also filter specifically by polarization or color/wavelength.

As shown in FIG. 4A, the subregions 411 and 413 are located close to a peripheral of the lens and substantially outside of a field of view of the user to reduce impact on the user's normal vision. The light source 401 and the subregions 411, 413 allow reflected light beams to form a spectrum of light having different wavelengths. The subregions 411, 413 can be coated using different formulas such that the light beams are selectively reflected by coatings on the ophthalmic lens. The combination of the light sources and dichroic coatings can produce reflected light in desired wavelength bands to provide corresponding therapeutical effects on the user.

In some embodiments, the light source(s) can be configured to emit light that is outside the visible light range, such as infrared light. In some embodiments, an antireflective coating can be deposited on the lens to interact with the back reflected light 415, thereby eliminating the back reflection.

Figure 4B:
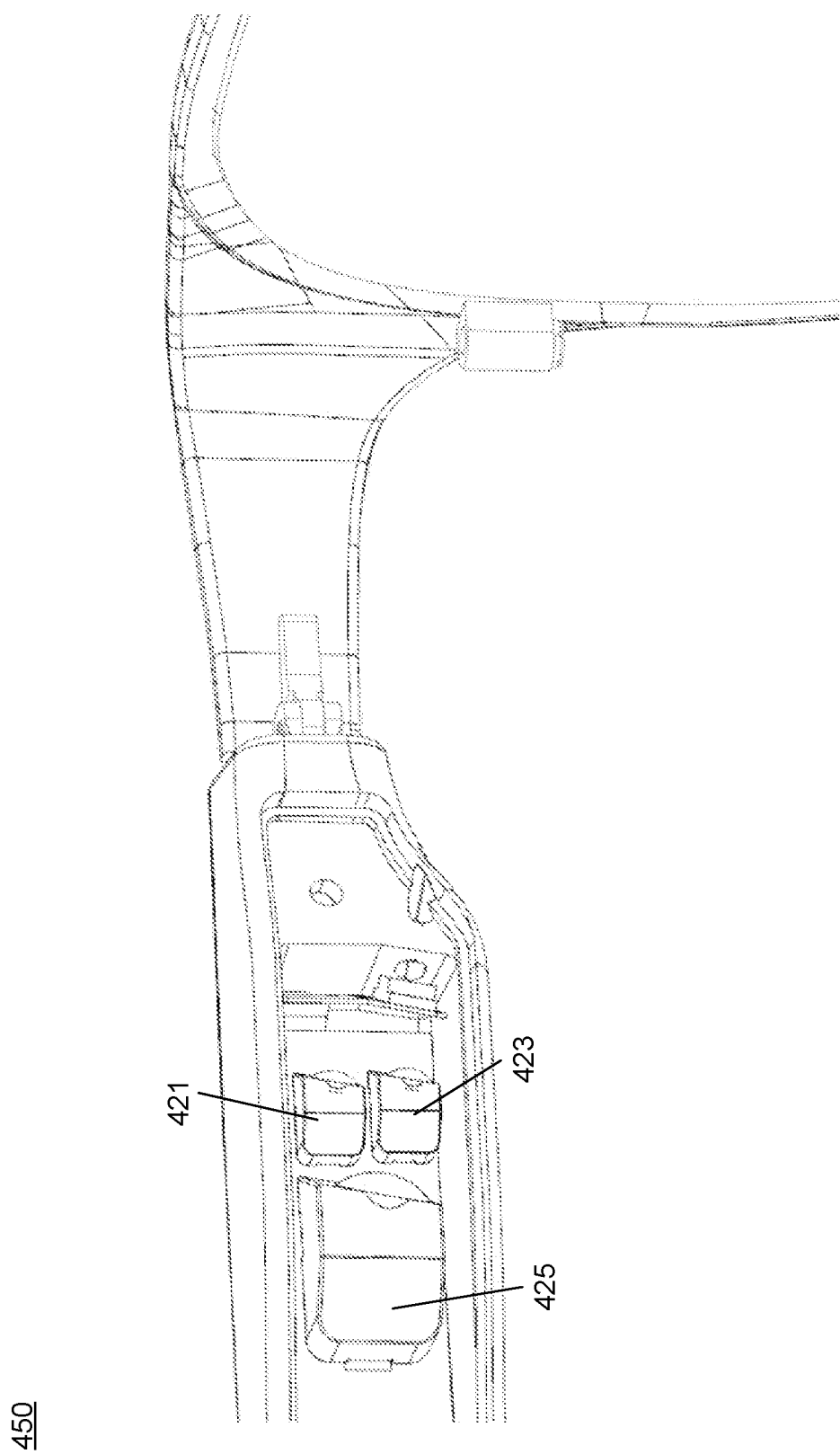
FIG. 4B illustrates another example configuration of multiple light sources coupled to a temple of an optical device in accordance with one or more embodiments of the present technology.

FIG. 4B illustrates another example configuration 450 of multiple light sources coupled to a temple of an optical device in accordance with one or more embodiments of the present technology. In this example, the protective cover is removed to expose the multiple light sources. The light sources are coupled to a corresponding temple of the frame. Each of the light sources comprises one or more lighting elements, such as Light Emitting Diodes (LEDs) or Liquid Crystal Displays (LCDs) backlit by one or more LED. In the specific example shown in FIG. 4B, each of the light sources 421 and 423 includes one LED. The light source 425 includes three LEDs. The individual LEDs are configured to output wavelengths specific to different intended treatments. For example, the three LEDs can be configured to emit light having different colors (e.g., yellow, green, blue) for different types of therapies/treatments. Blue light (e.g., ranging from 400-500 nm and peaking around 490 nm) can be more suitable to for circadian rhythm treatment while green light that is slightly below the most sensible range is more suitable for treatment of seasonal depression. The combination of the light sources (e.g., with different numbers of LEDs) can help achieve the desired treatment effects for the user.

In some embodiments, the ophthalmic lens can include a waveguide to produce the desired reflected light. A waveguide comprises a base substrate (e.g., glasses and/or the lenses) where light enters and travels through total internal reflection and is progressively coupled out of the substrate into the user's eyes while keeping the integrity of the original projection image. The waveguides serve as a method to expand the exit pupil of the display such that an image can be formed even when the location of the user's pupil changes relative to the guide. Some examples of waveguides include geometric waveguides, diffractive waveguides, holographic waveguides, and/or a combination of thereof. In addition, the base substrate can be either flat or curved.

Figure 5:
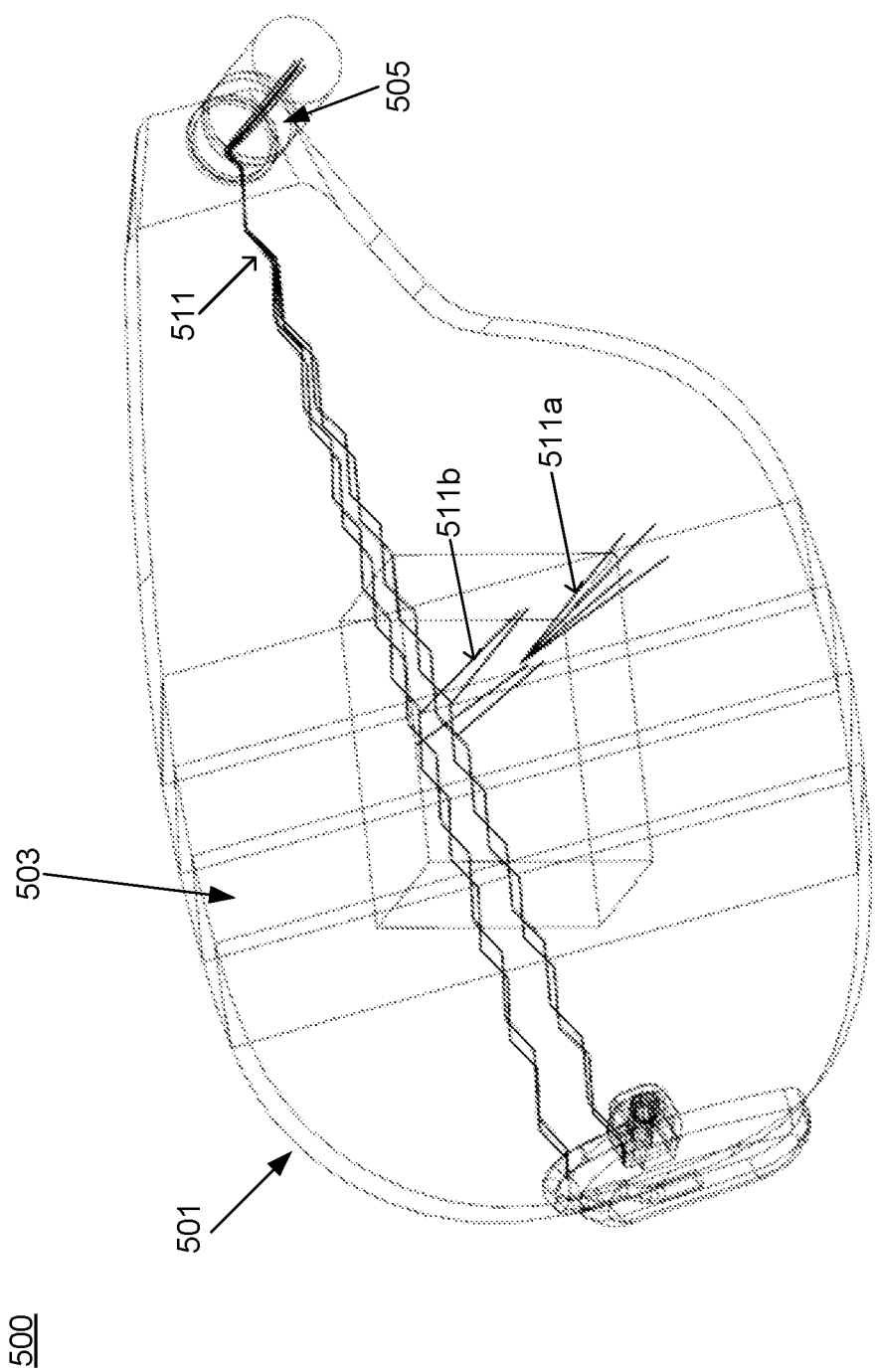
FIG. 5 illustrates an example configuration of a waveguide design in accordance with one or more embodiments of the present technology.

FIG. 5 illustrates an example configuration 500 of a waveguide design in accordance with one or more embodiments of the present technology. In this example, the ophthalmic lens 501 includes a set of surfaces embedded in it. The set of surfaces forms a waveguide 503 to progressively direct the light into the user's eyes. A light source 505 is positioned close to the ophthalmic lens (e.g., embedded in a temple of the frame) to emit light rays 511 into the lens 501.

In some embodiments, the light source is configured to generate collimated or partially collimated light rays to the waveguide. In this example, collimated light rays enter the lens in a substantially perpendicular manner and travel through total internal reflects before being directed to the user's pupil (511*a*, 511*b*) by the waveguide 503. For example, the light source can be positioned in a way that it projects at an angle to the waveguide, where the light traverses the space between the temples, the frames of the glasses, and/or the human eye/head. In some embodiments, the waveguide may not enforce the exact match of display to retina (e.g., 1:1 pixel matching/correspondence between the scene and eye perception) so long as important regions are projected with the correct colors for health and treatment purposes.

In some embodiments, before the light source enters the waveguide, a fraction of the light can be first reflected or filtered, e.g., via a reflective coating/film. The coating/film can be metal based, or holographic. For example, the fraction of reflected light can be directed towards the user's eyes for an initial form of treatment.

In some embodiments, geometric waveguide can be used to implement the disclosed techniques. The geometric waveguide can be coated with dichroic coatings such that it reflects only the incident angles between 10 to 30 degrees (e.g., preferably between 12 to 26 degrees) so as to minimize visual impact for straight viewing through the lenses. In some embodiments, the waveguide can be a diffractive waveguide (e.g., where the outcoupling features are very small surface geometry changes to allow change in direction) or a holographic waveguide (e.g., where three-dimensional geometries in the holographic film enables outcoupling of light from the internal reflection of the waveguide). In some embodiments, a holographic or diffractive waveguide can be arranged on other surface of the glasses, such as the inner or outer surface of the lens. In some embodiments, the waveguide can enable reflective surfaces through aluminum or silver on the lens, e.g., via thermal evaporation or sputter coating.

Figure 6A:
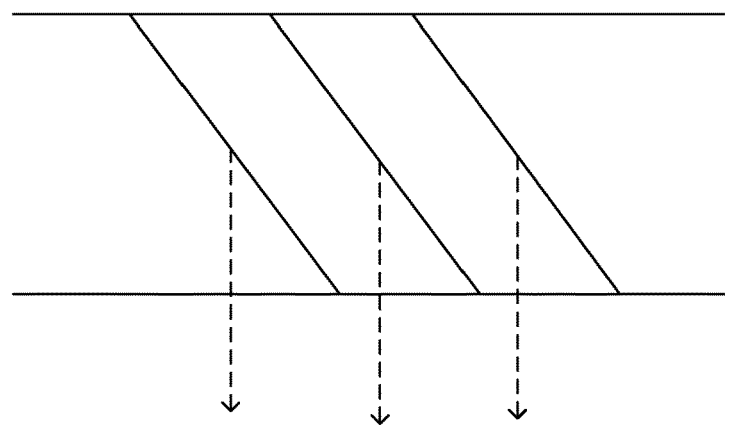
FIG. 6A illustrates an example of flat lens with parallel surfaces of a waveguide in accordance with one or more embodiments of the present technology.
Figure 6B:
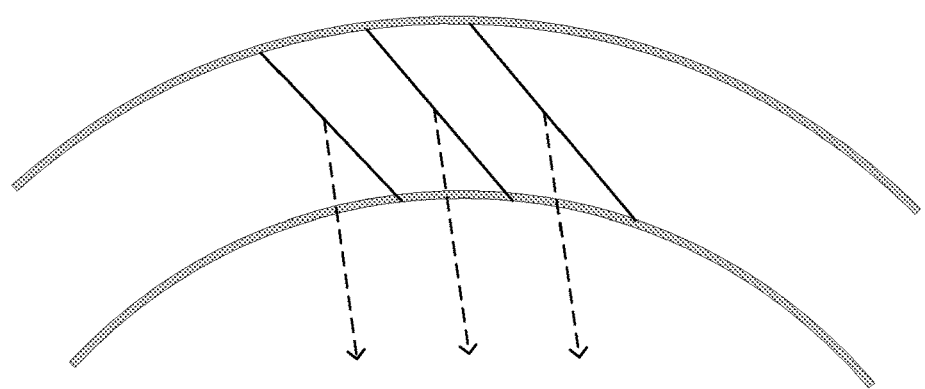
FIG. 6B illustrates an example of curved lens with parallel surfaces of a waveguide in accordance with one or more embodiments of the present technology.
Figure 6C:
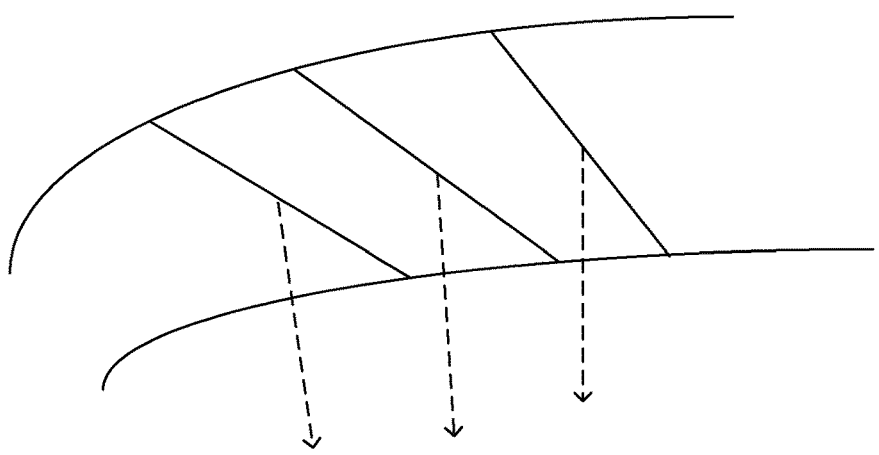
FIG. 6C illustrates an example of curved lens with non-parallel surfaces of a waveguide in accordance with one or more embodiments of the present technology.

In the example shown in FIG. 5, the waveguide includes parallel surfaces given the shape of the lens (e.g., flat surfaces of the lens). In other embodiments, the waveguide can include non-parallel surfaces (e.g., having varying angles with respect to the substrate) corresponding to curved lenses. FIGS. 6A-C illustrates different examples of lenses and waveguides in accordance with one or more embodiments of the present technology. FIG. 6A illustrates an example of flat lens with parallel surfaces of a waveguide in accordance with one or more embodiments of the present technology. FIG. 6B illustrates an example of curved lens with parallel surfaces of a waveguide in accordance with one or more embodiments of the present technology. In this example, the lens surfaces have consistent curvatures, therefore the use of parallel surfaces in the waveguide can properly direct the reflected light into the user's eyes. FIG. 6C illustrates an example of curved lens with non-parallel surfaces of a waveguide in accordance with one or more embodiments of the present technology. In this example, the surfaces of the lens have varying curvatures. Therefore, the waveguide includes non-parallel surfaces positioned to account for light with different incident angles for proper reflection.

In some embodiments, the optical device also includes a controller in communication with the light sources to control the operation of the light sources (e.g., turning a light source on/off, setting a schedule for the light source to be on, adjusting an intensity of the light source etc.). The controller can be coupled to the frame (e.g., positioned behind light sources as shown in FIGS. 4A-4B). In some embodiments, the output angle of the light sources can be adjusted via the controller such that a light source (e.g., including one or more LEDs) can be directed to different subregions of the ophthalmic lens coated using different materials. The flexible and adaptive combination of the light sources and the different coating regions enables a wide range of light therapies that can be performed on the user. In some embodiments, one or more batteries are also coupled to different components of the optical device (e.g., the controller and the light sources) to provide power to the optical device.

Figure 7:
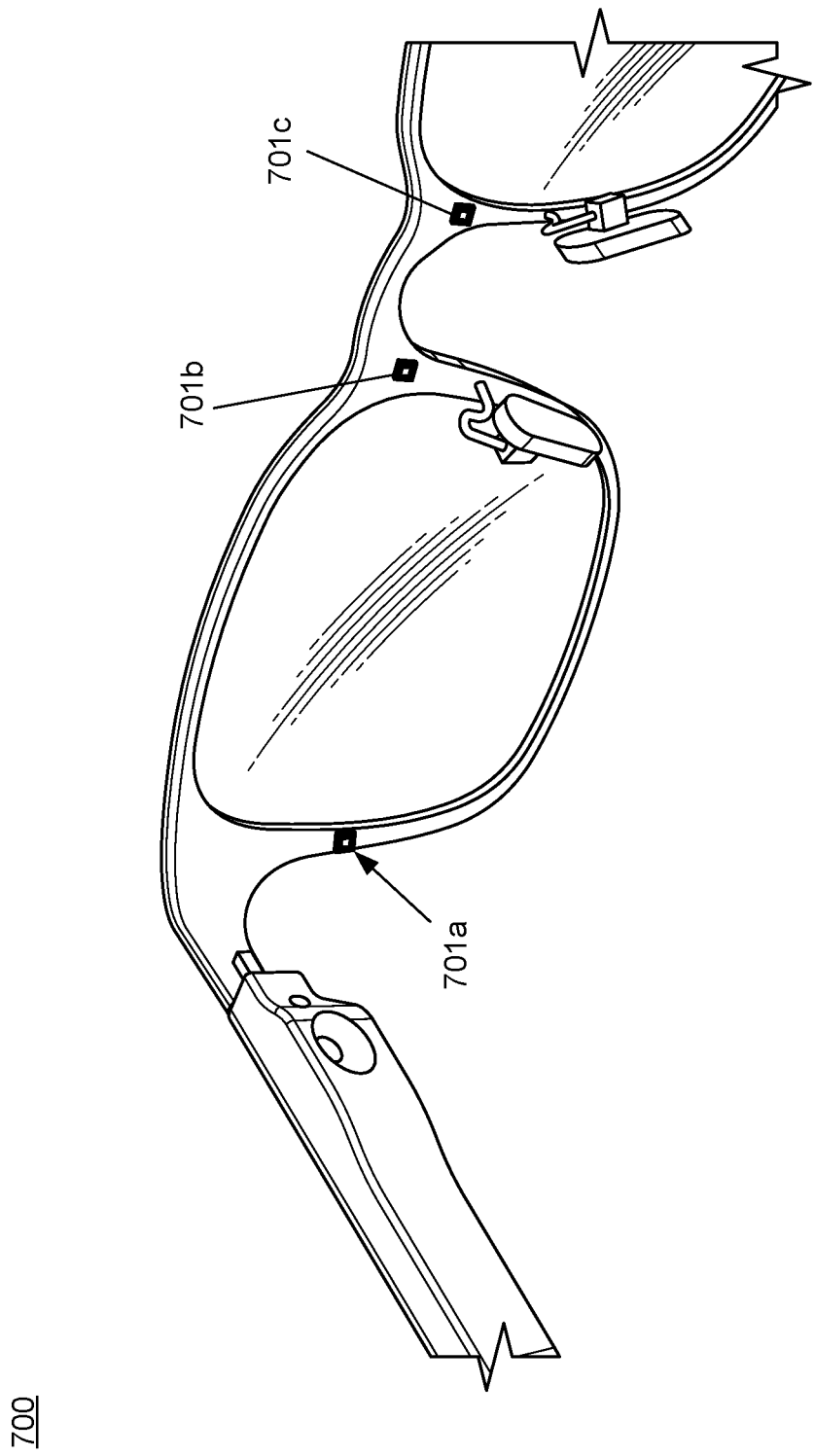
FIG. 7 illustrates an example optical device with one or more sensors in accordance with one or more embodiments of the present technology.

In some embodiments, the optical device includes one or more sensors that are configured to track an eye location and/or eye movement of the user. The one or more sensors are in communication with the controller so that the optical device can adaptively adjust, based on the detected eye movement by the sensors, the light output into the waveguide for an optimal location to place the projected light into the user's eyes. FIG. 7 illustrates an example optical device 700 with one or more sensors in accordance with one or more embodiments of the present technology. The sensor(s) 701*a-c* can be positioned on the frame of the optical device, facing the user, so as to detect the movement of the eyes. Based on the detected movement of the eye(s) or the pupil(s) (e.g., sleepiness, anxiety level, etc.), the controller of the optical device can adjust parameters of the light sources (e.g., by adaptively adjusting the light sources, such as the wavelength(s) of the light emitted, length and/or duration of the light emission) so as to adjust the light therapy performed on the user.

Figure 8:
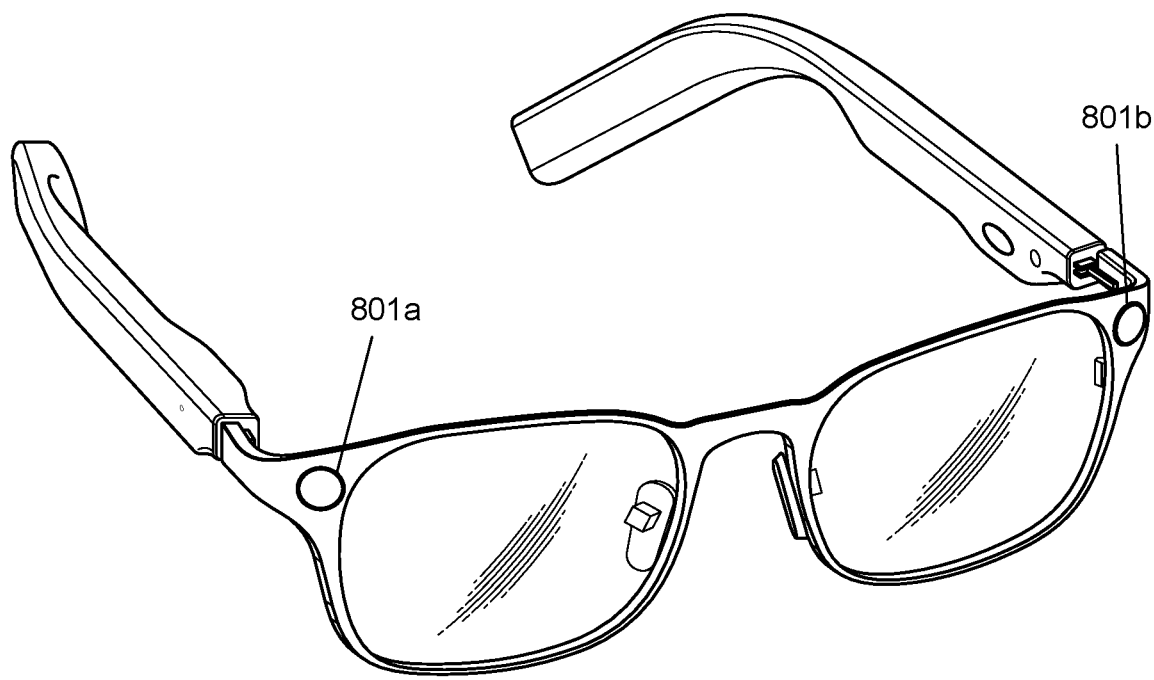
FIG. 8 illustrates an example optical device with one or more capturer in accordance with one or more embodiments of the present technology.

In some embodiments, the optical device includes a capturer model (e.g., camera) to collect information of the external environment so as to determine the ideal location/type of the therapy performed on the user. FIG. 8 illustrates an example optical device 800 with one or more capturer in accordance with one or more embodiments of the present technology. The capturer(s) 801*a*, 801*bb* can be implemented as cameras positioned on the frame of the optical device. The cameras 801*a-b* face outside towards the external environment to capture desired information. The capturer(s) 801*a-b* are in communication with the controller so that the controller can adjust parameters of the light sources (e.g., by adaptively adjusting the light sources, such as the wavelength(s) of the light emitted, length and/or duration of the light emission) so as to adjust the light therapy performed on the user.

Figure 9:
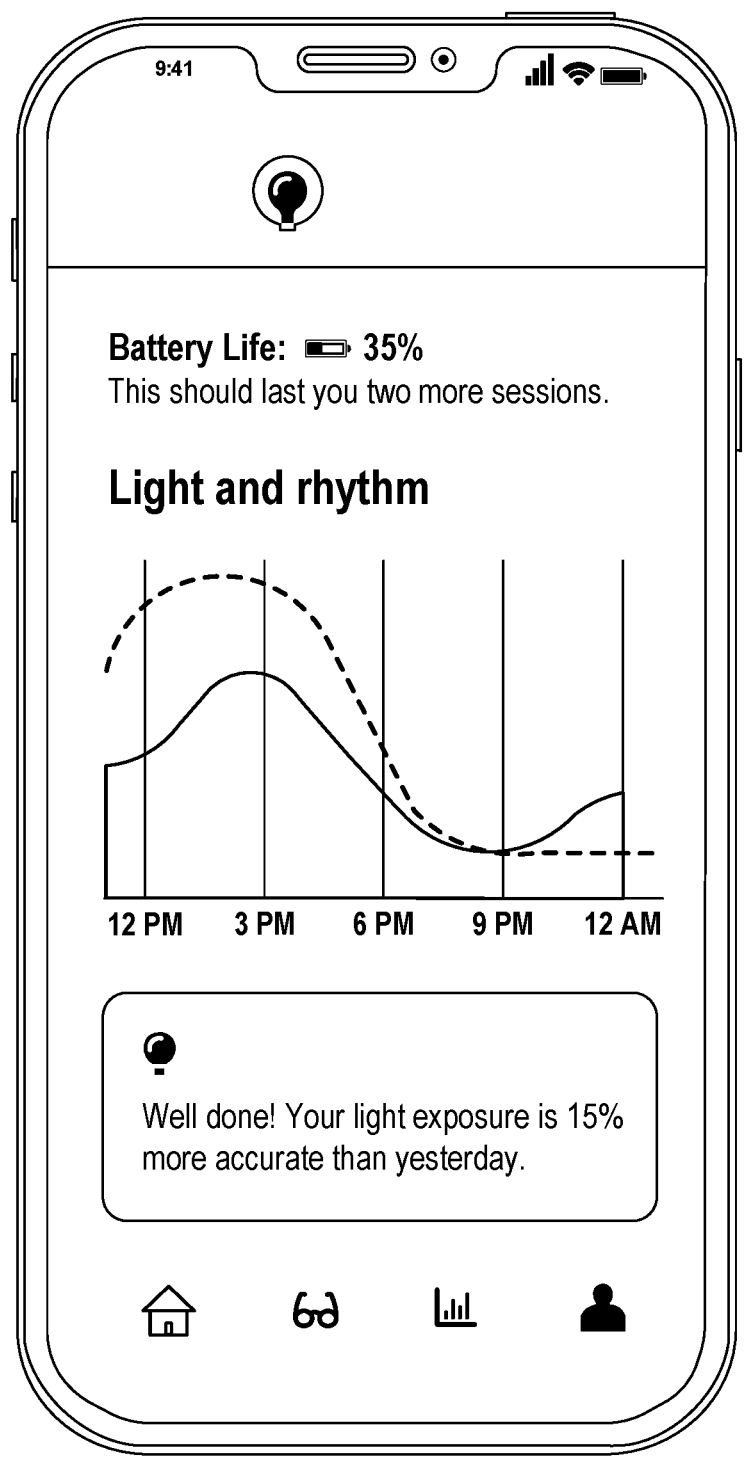
FIG. 9 illustrates an example user interface of a remote user device in accordance with one or more embodiments of the present technology.

In some embodiments, the controller includes a communication module (e.g., a Bluetooth module, a WiFi module, and/or a cellular module) that is in communication with one or more software programs deployed on a remote user device to facilitate control and adjustment of the light therapies. For example, an application can be deployed on a user device (e.g., a mobile phone or a tablet device) to allow the user to configure/change the parameters of the light therapies. FIG. 9 illustrates an example user interface of a remote user device in accordance with one or more embodiments of the present technology. For example, the user can adjust an intensity of the light sources via the user interface and the controller. As another example, the user can configure a schedule of light therapies throughout the day using different intensity of the light and/or different wavelengths to achieve the desired therapeutical effects. As yet another example, the light sources can be adjusted individually via a different tab on the user interface. In some embodiments, the system can monitor, via the controller of the optical device, a status of a battery of the optical device and notify the user to charge the battery when needed.

Figure 10:
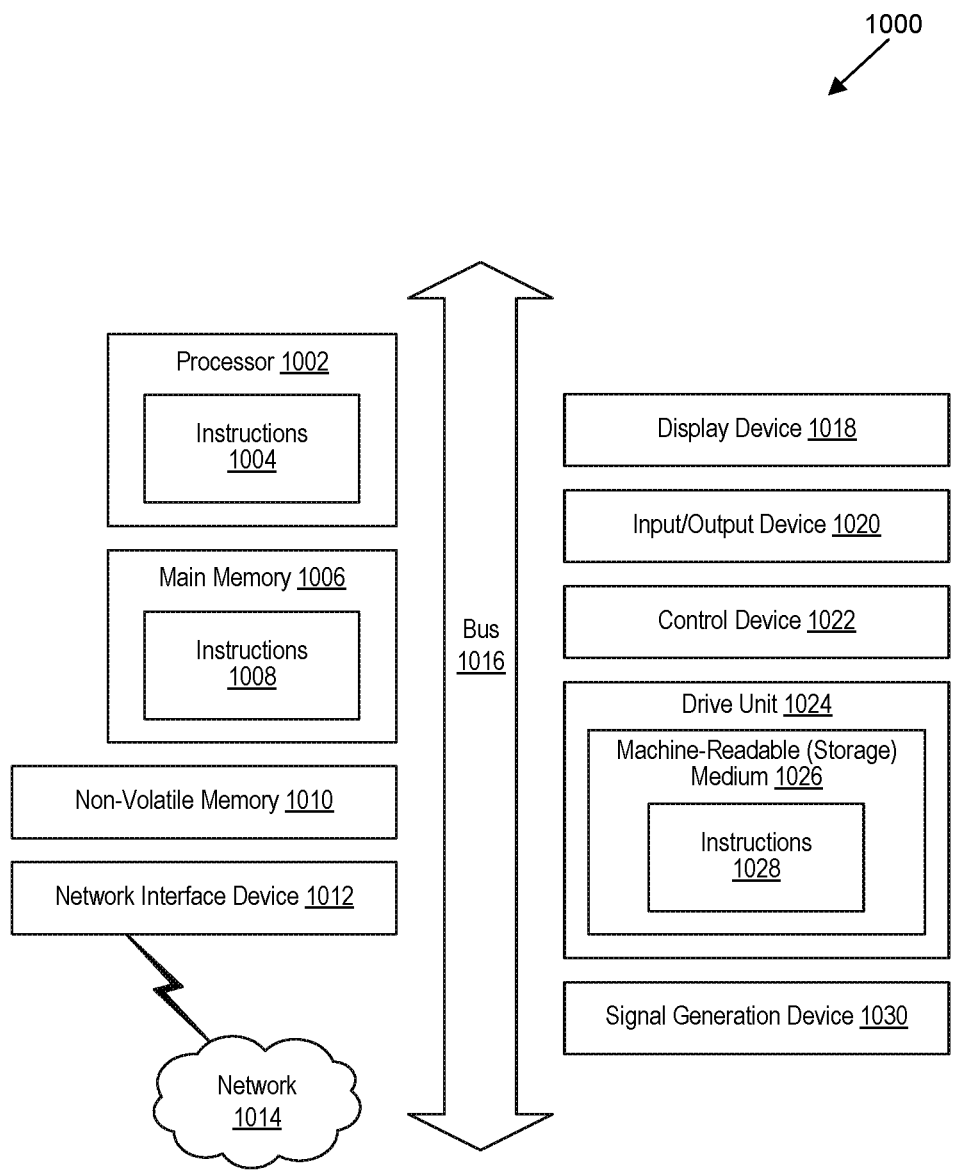
FIG. 10 is a block diagram that illustrates an example of a computing system in which at least some operations described herein can be implemented.

FIG. 10 is a block diagram that illustrates an example of a computing system 1000 in which at least some operations described herein (e.g., controller of the optical device, software programs deployed on remote user devices) can be implemented. As shown, the computing system 1000 can include: one or more processors 1002, main memory 1006, non-volatile memory 1010, a network interface device 1012, video display device 1018, an input/output device 1020, a control device 1022 (e.g., keyboard and pointing device), a drive unit 1024 that includes a storage medium 1026, and a signal generation device 1030 that are communicatively connected to a bus 1016. The bus 1016 represents one or more physical buses and/or point-to-point connections that are connected by appropriate bridges, adapters, or controllers. Various common components (e.g., cache memory) are omitted from FIG. 10 for brevity. Instead, the computing system 1000 is intended to illustrate a hardware device on which components illustrated or described relative to the examples of the figures and any other components described in this specification can be implemented.

The computing system 1000 can take any suitable physical form. For example, the computing system 1000 can share a similar architecture as that of a server computer, personal computer (PC), tablet computer, mobile telephone, game console, music player, wearable electronic device, network-connected ("smart") device (e.g., a television or home assistant device), AR/VR systems (e.g., head-mounted display), or any electronic device capable of executing a set of instructions that specify action(s) to be taken by the computing system 1000. In some implementation, the computing system 1000 can be an embedded computing system, a system-on-chip (SOC), a single-board computer system (SBC) or a distributed system such as a mesh of computing systems or include one or more cloud components in one or more networks. Where appropriate, one or more computing systems 1000 can perform operations in real-time, near real-time, or in batch mode.

The network interface device 1012 enables the computing system 1000 to mediate data in a network 1014 with an entity that is external to the computing system 1-00 through any communication protocol supported by the computing system 1000 and the external entity. Examples of the network interface device 1012 include a network adaptor card, a wireless network interface card, a router, an access point, a wireless router, a switch, a multilayer switch, a protocol converter, a gateway, a bridge, bridge router, a hub, a digital media receiver, and/or a repeater, as well as all wireless elements noted herein.

The memory (e.g., main memory 1006, non-volatile memory 1010, machine-readable medium 1026) can be local, remote, or distributed. Although shown as a single medium, the machine-readable medium 1026 can include multiple media (e.g., a centralized/distributed database and/or associated caches and servers) that store one or more sets of instructions 1028. The machine-readable (storage) medium 1026 can include any medium that is capable of storing, encoding, or carrying a set of instructions for execution by the computing system 1000. The machine-readable medium 1026 can be non-transitory or comprise a non-transitory device. In this context, a non-transitory storage medium can include a device that is tangible, meaning that the device has a concrete physical form, although the device can change its physical state. Thus, for example, non-transitory refers to a device remaining tangible despite this change in state.

Although implementations have been described in the context of fully functioning computing devices, the various examples are capable of being distributed as a program product in a variety of forms. Examples of machine-readable storage media, machine-readable media, or computer-readable media include recordable-type media such as volatile and non-volatile memory devices 1010, removable flash memory, hard disk drives, optical disks, and transmission-type media such as digital and analog communication links.

In general, the routines executed to implement examples herein can be implemented as part of an operating system or a specific application, component, program, object, module, or sequence of instructions (collectively referred to as "computer programs"). The computer programs typically comprise one or more instructions (e.g., instructions 1004, 1008, 1028) set at various times in various memory and storage devices in computing device(s). When read and executed by the processor 1002, the instruction(s) cause the computing system 1000 to perform operations to execute elements involving the various aspects of the disclosure.

Figure 11:
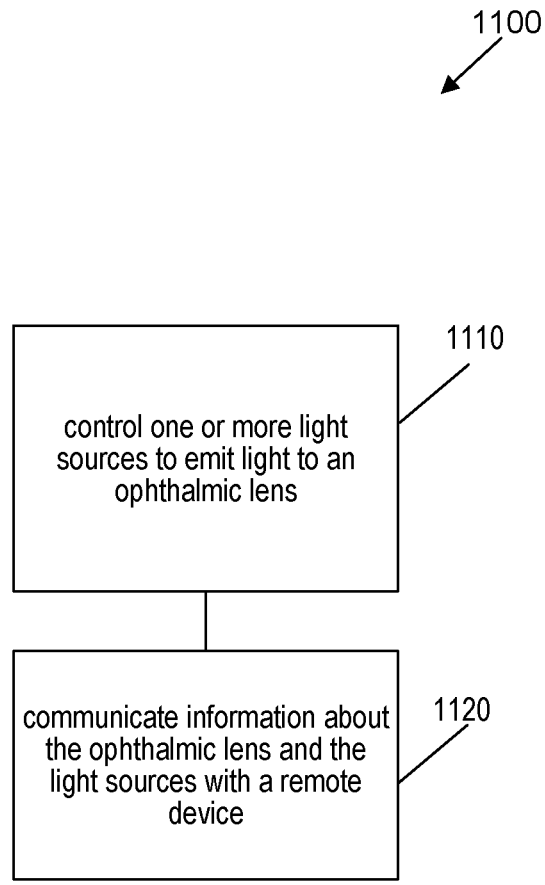
FIG. 11 is a flowchart representation of a method for providing a light therapy to a user in accordance with one or more embodiments of the present technology.

FIG. 11 is a flowchart representation of a method 1100 for providing a light therapy to a user using an optical device in accordance with one or more embodiments of the present technology. The optical device comprises an ophthalmic lens, a coating deposited in multiple sub-regions of the ophthalmic lens, a frame with two temples, and a light source coupled to each of the two temples of the frame (e.g., as shown in FIG. 1A). The light source is controllable to emit light directed at the coating of the ophthalmic lens such that a portion of the light reflected by the multiple regions of the ophthalmic lens forms a spectrum of light that has different wavelength bands corresponding to different therapeutical effects on the user (e.g., as shown in FIG. 2B). The method includes, at operation 1110, controlling, via a controller of the optical device, the light source to emit light to the ophthalmic lens such that a portion of the light is reflected by the ophthalmic lens into a pupil of the user. The method also includes, at operation 1120, communicating information about the ophthalmic lens and the multiple light sources with a remote device to enable the user to track a performance of the light therapy on the remote device.

In some embodiments, the different therapeutical effects comprise at least a first therapeutical effect related to circadian rhythm or sleep, and a second circadian rhythm related to depression. For example, a peak wavelength of one of the multiple light sources can be within a range between 490 nm and 495 nm. In some embodiments, one of the different wavelength bands is at least partially outside of a visible spectrum.

In some embodiments, the method includes filtering, via a filter (e.g., filter 417) positioned between the light source and the ophthalmic lens, light from the light source before the light reaches the ophthalmic lens. In some embodiments, the optical device comprises a set of surfaces embedded in the ophthalmic lens, and the method includes adaptively adjusting a first light source of the multiple light sources to emit light into the ophthalmic lens such that the light enters a first side of the ophthalmic lens and is progressively reflected back to the user by the set of surfaces in the ophthalmic lens. In some embodiments, the set of surfaces includes at least one surface that is not parallel to remaining surfaces in the set (e.g., as shown in FIGS. 6A-C). In some embodiments, the set of surfaces comprises a dichroic coating to reflect light with an incident angle between 12 to 26 degrees. In some embodiments, the set of surfaces comprises a diffractive waveguide or a holographic waveguide.

In some embodiments, the method includes detecting, by a sensor of the optical device, a movement of a pupil of the user and adaptively adjusting one of the multiple light sources based on the movement of the pupil of the user. In some embodiments, the method includes adjusting, via the controller of the optical device, an intensity of one of the multiple light sources coupled to each of the two temples of the frame. In some embodiments, the method includes scheduling, via the controller of the optical device, a length of operation of one of the multiple light sources coupled to each of the two temples of the frame. In some embodiments, the method includes monitoring, via the controller of the optical device, a status of a battery of the optical device. In some embodiments, the method includes capturing, via a capture module of the optical device, information about an external environment of the user.

The disclosed techniques further embody the manufacturing process for applying dichroic coatings onto ophthalmic lenses, which present special considerations in the coating deposition process.

An embodiment of the invented process comprises a machine or device that provides the deposition. The machine maintains the pressure of the deposition chamber that accounts for outgassing of the ophthalmic lens substrate. An example is to maintain the pressure at 5.5 E-3 Pa such that it provides a partial vacuum that is sufficient for a clean deposition, while controlling for outgassing of the substrate. Note that 5.5 E-3 Pa is only an example pressure. Depending on the nature of the ophthalmic lens substrate and environment conditions, the vacuum pressure maintained may be different.

Furthermore, temperature of the process and substrate may also be controlled to ensure good surface bonding, yet not cause melting of the overall substrate. One method to control the temperature is by slowing down the ion blasting process, such as turning on the ion blasting process only when the substrate temperature is below a threshold and turning off the blaster when the temperature is above a second threshold. Other temperature control methods may be used to achieve the same effect. The ophthalmic lens substrate can be machined prior or after the coating process. In addition, the substrate, either machined un machined, may be cleaned, polished, and examined for surface defects before being fixed into the machine via fixtures for dichroic coating deposition.

Example solutions that implement the disclosed techniques include at least the following:

Solution 1. An optical device comprises an ophthalmic lens; a frame comprising a frame front configured to support the ophthalmic lens, the frame comprising two temples configured to allow a user to wear the optical device; and a coating that is deposited in multiple sub-regions of the ophthalmic lens. The multiple sub-regions are coated using different coating formulas, and the multiple sub-regions are located close to a peripheral of the ophthalmic lens and substantially outside of a field of view of a user of the optical device. The device comprises a light source coupled to each of the two temples of the frame. The light source is controllable to emit a light beam directed at the coating of the ophthalmic lens such that a portion of the light beam reflected by the multiple sub-regions of the ophthalmic lens forms a spectrum of light that has different wavelength bands corresponding to different therapeutical effects on the user. When the optical device is in operation, the spectrum of light is reflected into a pupil of the user as part of a light therapy session.

2. The optical device of solution 1, wherein the different therapeutical effects comprise at least one of: a first therapeutical effect related to circadian rhythm or sleep, or a second circadian rhythm related to depression.

3. The optical device of solution 1 or 2, wherein a peak wavelength of the light beam from the light source is around 490 nm.

4. The optical device of any of solution 1 to 3, comprising: a filter positioned between the light source and the ophthalmic lens, wherein the filter is configured to filter light from the light source before the light reaches the ophthalmic lens.

5. The optical device of any of solution 1 to 4, further comprising: a sensor coupled to the frame configured to track a movement of the pupil of the user. The light source is adaptively adjusted based on the movement of the pupil detected by the sensor.

6. The optical device of any of solution 1 to 5, further comprising: a controller in communication with the light source to control an operation of the light source.

7. The optical device of solution 6, wherein the controller comprises a communication module that is configured to exchange information about the ophthalmic lens and the light source coupled to each of the two temples with a remote device.

8. The optical device of solution 6 or 7, wherein the controller is configured to adjust an intensity of the light source coupled to each of the two temples of the frame.

9. The optical device of any of solution 6 to 9, wherein the controller is configured to schedule a length of operation of the light source coupled to each of the two temples of the frame.

10. The optical device of any of solution 6 to 9, further comprising: a battery embedded in the frame, wherein the controller is coupled to the battery to monitor of a status of the battery.

11. The optical device of any of solution 1 to 10, further comprising: a capture module configured to capture information about an external environment of the user.

12. The optical device of any of solution 1 to 11, wherein the frame is foldable or collapsible.

13. An optical device, comprising: an ophthalmic lens; a frame comprising a frame front configured to support the ophthalmic lens, the frame comprising two temples configured to allow a user to wear the optical device; a coating that is deposited in at least one sub-region of the ophthalmic lens. The at least one sub-region is located close to a peripheral of the ophthalmic lens and substantially outside of a field of view of a user of the optical device. The multiple light sources coupled to each of the two temples of the frame. The multiple light sources are individually controllable to emit light beams directed at the coating of the ophthalmic lens such that a portion of the light beams reflected by the at least one sub-region of the ophthalmic lens forms a spectrum of light that has different wavelength bands corresponding to different therapeutical effects on the user. When the optical device is in operation, the spectrum of light is reflected into a pupil of the user as part of a light therapy session.

14. The optical device of solution 13, wherein one of the different wavelength bands is at least partially outside of a visible spectrum.

15. The optical device of solution 13 or 14, further comprising: a set of surfaces embedded in the ophthalmic lens, wherein the light source is adaptively adjustable to emit light into the ophthalmic lens such that the light enters a first side of the ophthalmic lens and is progressively reflected back to the user by the set of surfaces in the ophthalmic lens.

16. The optical device of solution 15, wherein the set of surfaces comprises a dichroic coating to reflect light with an incident angle between 12 to 26 degrees.

17. The optical device of solution 15 or 16, wherein the set of surfaces comprises a diffractive waveguide or a holographic waveguide.

18. A method of providing a light therapy to a user, comprising: controlling, via a controller of an optical device, a light source of the optical device to emit light to an ophthalmic lens of the optical device such that a portion of the light is reflected by the ophthalmic lens into a pupil of the user. The optical device comprises the ophthalmic lens, a coating deposited in multiple sub-regions of the ophthalmic lens, a frame with two temples, and the light source coupled to each of the two temples of the frame. The light source is controllable to emit a light beam directed at the coating of the ophthalmic lens such that a portion of the light beam reflected by the multiple sub-regions of the ophthalmic lens forms a spectrum of light that has different wavelength bands corresponding to different therapeutical effects on the user. The method comprises communicating, via a communication model of the optical device, information about the ophthalmic lens and the light source with a remote device to enable the user to track a performance of the light therapy on the remote device.

19. The method of solution 18, wherein the different therapeutical effects comprise at least a first therapeutical effect related to circadian rhythm or sleep, and a second circadian rhythm related to depression.

20. The method of solution 18 or 19, wherein a peak wavelength of the light source is within a range between 490 nm and 495 nm.

21. The method of any of solution 18 to 20, comprising: filtering, via a filter positioned between the light source and the ophthalmic lens, light from a light source before the light reaches the ophthalmic lens.

22. The method of any of solution 18 to 21, wherein the optical device comprises a set of surfaces embedded in the ophthalmic lens, the method comprising: adaptively adjusting, via the controller of the optical device, the light source to emit light into the ophthalmic lens such that the light enters a first side of the ophthalmic lens and is progressively reflected back to the user by the set of surfaces in the ophthalmic lens.

23. The method of solution 22, wherein the set of surfaces includes at least one surface that is not parallel to remaining surfaces in the set.

24. The method of solution 22 or 23, wherein the set of surfaces comprises a dichroic coating to reflect light with an incident angle between 12 to 26 degrees.

25. The method of any of solution 22 to 24, wherein the set of surfaces comprises a diffractive waveguide or a holographic waveguide.

26. The method of any of solution 18 to 25, comprising: detecting, by a sensor of the optical device, a movement of the pupil of the user; and adaptively adjusting the light source based on the movement of the pupil of the user.

27. The method of any of solution 18 to 26, comprising: adjusting, via the controller of the optical device, an intensity of the light source coupled to each of the two temples of the frame.

28. The method of any of solution 18 to 27, comprising: scheduling, via the controller of the optical device, a length of operation of the light source coupled to each of the two temples of the frame.

29. The method of any of solution 18 to 28, comprising: monitoring, via the controller of the optical device, a status of a battery of the optical device.

30. The method of any of claims 18 to 29, comprising: capturing, via a capture module of the optical device, information about an external environment of the user.

31. A method of coating one or more sub-regions of an ophthalmic lens, comprising: positioning a lens in a chamber; controlling a temperature of the chamber via an ion blasting process, wherein the controlling comprises turning on the ion blasting process upon the temperature being lower than a first threshold and turning off the blasting processing upon the temperature exceeding a second threshold; and performing a vapor deposition of a dichroic coating on the one or more sub-regions of the lens.

Solution 32. An application of depositing dichroic wavelength selective coatings on ophthalmic lenses for light therapy.

33. The method of depositing dichroic coatings on ophthalmic lenses according to solution 1, where a vapor deposition machine or device can be used to apply the coating.

34. A calculation method can be used to prepare the dichroic coating formula for deposition according to solution 32, where the calculation can account for phototherapy requirements, coating properties, prescription, refractive indexes, and lens geometries.

35. The machine or device according to solution 2 may include an ion beam blasting process to surface treat the ophthalmic lens substrate during the coating process 36. The vapor deposition machine or device according to solution 33, where the environment pressure may be controlled to provide a partial vacuum that prevents the substrate and coating materials from experiencing too much outgassing while providing adequate vacuum for clean deposition.

37. The machine or device according to solution 33 may include a temperature control method to ensure the average temperature of the substrate stays below its melting point.

38. The temperature control method according to solution 37, where temperature may be controlled by reducing the intensity of the beam blasting 39. The beam blasting intensity reduction method according to solution 38, where the ion beam may be turned on and off based on various temperature thresholds 40. The ophthalmic lenses according to solution 32 may be machined prior and after the coating process to achieve its final form factor 41. The machined ophthalmic lenses according to solution 40, where a polishing process may be used on the substrate before and/or after the coating process to enable a clean surface 42. The deposition machine or device according to solution 33, where a fixture may be used to position the lens substrate during the coating process 43. The deposition of the coating on the lenses, where the lens can be partially coated, or be a combination of different wavelength-based coatings based on the location of the lens.
44. The partial deposition of the coating on the lenses according to solution 43, where the partial coating may be achieved through masking during the deposition process
45. The application of coating on the lenses, where the coating can be first deposited onto a substrate and the substrate is later assembled or adhered onto the ophthalmic lenses
46. The application of coating on the lenses, where the coating can be first deposited onto lens subdivisions and the subdivisions are joined together to form the full ophthalmic lens.

Various operations disclosed herein can be implemented using a processor/controller is configured to include, or be couple to, a memory that stores processor executable code that causes the processor/controller carry out various computations and processing of information. The processor/controller can further generate and transmit/receive suitable information to/from the various system components, as well as suitable input/output (IO) capabilities (e.g., wired or wireless) to transmit and receive commands and/or data.

Various information and data processing operations described herein may be implemented in one embodiment by a computer program product, embodied in a computer-readable medium, including computer-executable instructions, such as program code, executed by computers in networked environments. A computer-readable medium may include removable and non-removable storage devices including, but not limited to, Read Only Memory (ROM), Random Access Memory (RAM), compact discs (CDs), digital versatile discs (DVD), etc. Therefore, the computer-readable media that is described in the present application comprises non-transitory storage media. Generally, program modules may include routines, programs, objects, components, data structures, etc. that perform particular tasks or implement particular abstract data types. Computer-executable instructions, associated data structures, and program modules represent examples of program code for executing steps of the methods disclosed herein. The particular sequence of such executable instructions or associated data structures represents examples of corresponding acts for implementing the functions described in such steps or processes.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. An optical device, comprising:
   an ophthalmic lens;
   a frame comprising a frame front configured to support the ophthalmic lens, the frame comprising two temples configured to allow a user to wear the optical device;
   a coating that is deposited in multiple sub-regions of the ophthalmic lens,
   wherein the multiple sub-regions are coated using different coating formulas, and
   wherein the multiple sub-regions are located close to a peripheral of the ophthalmic lens and substantially outside of a field of view of the user of the optical device; and
   a light source coupled to each of the two temples of the frame,
   wherein the light source is controllable to emit a light beam directed at the coating of the ophthalmic lens such that a portion of the light beam reflected by the multiple sub-regions of the ophthalmic lens forms a spectrum of light that has different wavelength bands corresponding to different therapeutical effects on the user;
   wherein, when the optical device is in operation, the spectrum of light is reflected into a pupil of the user as part of a light therapy session.

2. The optical device of claim 1, wherein the different therapeutical effects comprise at least one of: a first therapeutical effect related to circadian rhythm or sleep, or a second therapeutical effect related to depression.

3. The optical device of claim 1, wherein a peak wavelength of the light beam from the light source is in a range between 490 nm and 495 nm.

4. The optical device of claim 1, comprising:
   a filter positioned between the light source and the ophthalmic lens, wherein the filter is configured to filter light from the light source before the light reaches the ophthalmic lens.

5. The optical device of claim 1, further comprising:
   a sensor coupled to the frame configured to track a movement of the pupil of the user,
   wherein the light source is adaptively adjusted based on the movement of the pupil detected by the sensor.

6. The optical device of claim 1, further comprising:
   a controller in communication with the light source to control an operation of the light source.

7. The optical device of claim 6, wherein the controller comprises a communication module that is configured to exchange information about the ophthalmic lens and the light source coupled to each of the two temples with a remote device.

8. The optical device of claim 6, wherein the controller is configured to adjust an intensity of the light source coupled to each of the two temples of the frame.

9. The optical device of claim 6, wherein the controller is configured to schedule a length of the operation of the light source coupled to each of the two temples of the frame.

10. The optical device of claim 6, further comprising:
    a battery embedded in the frame, wherein the controller is coupled to the battery to monitor of a status of the battery.

11. The optical device of claim 1, further comprising:
a capture module configured to capture information about an external environment of the user.

12. The optical device of claim 1, wherein the frame is foldable or collapsible.

13. An optical device, comprising:
an ophthalmic lens;
a frame comprising a frame front configured to support the ophthalmic lens, the frame comprising two temples configured to allow a user to wear the optical device;
a coating that is disposed in multiple sub-regions of the ophthalmic lens,
wherein the multiple sub-regions are coated using different coating formulas configured to reflect light in different wavelength bands, and
wherein the multiple sub-regions are located close to a peripheral of the ophthalmic lens and substantially outside of a field of view of the user of the optical device; and
a light source coupled to each of the two temples of the frame,
wherein the light source is controllable to emit a light beam directed at the coating of the ophthalmic lens such that a portion of the light beam is reflected into a pupil of the user, the portion of the light beam reflected by the multiple sub-regions of the ophthalmic lens forming a spectrum of light having the different wavelength bands.

14. The optical device of claim 13, wherein the different wavelength bands comprise at least one of: a blue light band in a range of 450-550 nm, or a green light band in a range of 465-625 nm.

15. The optical device of claim 13, wherein a peak wavelength of the light beam from the light source is in a range between 490 nm and 495 nm.

16. The optical device of claim 13, wherein at least one of the different coating formulas comprises at least one of: Silicone Oxide ($S_iO_2$), Magnesium Fluoride ($M_gF_2$), Titanium Oxide, or Zirconium Oxides.

17. The optical device of claim 13, comprising:
a protective cover coupled to the frame,
wherein the light source is positioned behind the protective cover.

18. The optical device of claim 17, wherein the protective cover comprises a filter that is configured to filter light from the light source before the light reaches the ophthalmic lens.

19. The optical device of claim 13, further comprising:
a sensor coupled to the frame configured to track a movement of the pupil of the user,
wherein the light source is adaptively adjusted based on the movement of the pupil detected by the sensor.

20. The optical device of claim 13, further comprising:
a controller in communication with the light source to control an operation of the light source.

21. The optical device of claim 20, wherein the controller comprises a communication module that is configured to exchange information about the ophthalmic lens and the light source coupled to each of the two temples with a remote device,
wherein the controller is configured to adjust an intensity of the light source coupled to each of the two temples of the frame.

* * * * *